US007863330B2

(12) United States Patent
Makovec et al.

(10) Patent No.: US 7,863,330 B2
(45) Date of Patent: Jan. 4, 2011

(54) DELOXIGLUMIDE AND PROTON PUMP INHIBITOR COMBINATION IN THE TREATMENT OF GASTROINTESTINAL DISORDERS

(75) Inventors: Francesco Makovec, Lesmo (IT); Massimo Maria D'Amato, Monza (IT); Antonio Giordani, Pavia (IT); Lucio Claudio Rovati, Monza (IT)

(73) Assignee: Rottapharm S.p.A., Milan (IT)

( * ) Notice: Subject to any disclaimer, the term of this patent is extended or adjusted under 35 U.S.C. 154(b) by 0 days.

(21) Appl. No.: 11/424,104

(22) Filed: Jun. 14, 2006

(65) Prior Publication Data

US 2007/0293574 A1 Dec. 20, 2007

(51) Int. Cl.
*A61K 31/192* (2006.01)
*A61K 31/197* (2006.01)
*A61K 31/4184* (2006.01)

(52) U.S. Cl. .................................... 514/564; 514/395

(58) Field of Classification Search ........................ None
See application file for complete search history.

(56) References Cited

U.S. PATENT DOCUMENTS

| 4,255,431 A | 3/1981 | Junggren et al. |
| 4,628,098 A | 12/1986 | Nohara et al. |
| 4,758,579 A | 7/1988 | Kohl et al. |
| 4,769,389 A | 9/1988 | Makovec et al. |
| 4,880,938 A | 11/1989 | Freidinger |
| 5,045,552 A | 9/1991 | Souda et al. |
| 5,130,474 A | 7/1992 | Makovec et al. |
| 5,693,818 A | 12/1997 | Von Unge |

FOREIGN PATENT DOCUMENTS

| WO | WO 93/12817 | 7/1993 |
| WO | WO 01/85167 A1 | 11/2001 |
| WO | WO 01/85704 A1 | 11/2001 |
| WO | WO 01/85723 A1 | 11/2001 |
| WO | WO 01/85724 A1 | 11/2001 |
| WO | WO 01/90078 A1 | 11/2001 |
| WO | WO 03/041714 A1 | 5/2003 |
| WO | WO 2004/098609 A1 | 11/2004 |
| WO | WO 2004/098610 A1 | 11/2004 |
| WO | WO 2004/101533 A1 | 11/2004 |
| WO | WO 2004/105795 A1 | 12/2004 |
| WO | WO 2005/074931 A1 | 8/2005 |

OTHER PUBLICATIONS

Boeckxstaens, G.E.E., Current Treatment Options in Gastroenterology (2001), 4:317-322.*
Barclay, L., Drugs in Clinical Trials (Apr. 2005), www.centerwatch.com/professional/cwpipeline/eyeon_gerd.html.*
The Merck Index, 17th edition (1999), pp. 221-223.*
Persiani et al., Clinical Pharmacokinetics, 45(12), (2006), pp. 1177-1188 (abstract).*

Holstein et al., MI1437, AZD0865—A New Potassium-Competitive Acid Blocker—Exhibits Maximal Gastric Antisecretory Effects from First Dose, AGA Abstracts, p. A-333.
Borovicka et al., "Role of cholecystokinin as a regulator of solid and liquid gastric emptying in humans", Am. J. Physiol. 271 (Gastrointest. Liver Physiol . 34): G448-G453, 1996.
Chua et al., "Cholecystokinin Hyperresponsiveness in Dysmotility-Type Nonulcer Dyspepsia"; pp. 298-299.
Chua et al., "Clinical Efficacy and Prokinetic Effect of the CCK-A Antagonist Loxiglumide in Nonulcer Dyspepsia", Cholecystokinin, Annals of the New York Academy of Sciences, Mar. 23, 1994, vol. 713, pp. 451-453.
Feinle et al., "Cholecystokinin-A Receptors Modulate Gastric Sensory and Motor Responses to Gastric Distention and Duodenal Lipid", Gastroenterology 1996, vol. 110, pp. 1379-1385.
Feinle et al., "Role of duodenal lipid and cholecystokinin A receptors in the pathophysiology of functional dyspepsia", Gut 2001, vol. 48, pp. 347-355.
Katschinski et al., "Intestinal phase of human antro-pyloro-duodenal motility: cholinergic and CCK-mediated regulation", European Journal of Clinical Investigation (1996), vol. 26, pp. 574-583.
Lal et al., "Cholecystokinin pathways modulate sensations induced by gastric distension in humans"; Am. J. Physiol. Gastrointest Liver Physiol. 287; pp. G72-G79; 2004.
Lassen et al., "Helicobacter pylori test-and-eradicate versus prompt endoscopy for management of dyspeptic patients: a randomised trial", The Lancet, vol. 356, Aug. 5, 2000, pp. 455-460.
Locke et al., "Prevalence and Clinical Spectrum of Gastroesophageal Reflux: A Population-Based Study in Olmsted County, Minnesota", Gastroenterology 1997; vol. 112, pp. 1448-1456.
Schwizer et al., "Role of cholecystokinin in the regulation of liquid gastric emptying and gastric motility in humans: studies with the CCK antagonist loxiglumide", Gut 1997, vol. 41, pp. 500-504.
Tougas et al., "Prevalence and Impact of Upper Gastrointestinal Symptoms in the Canadian Population: Findings From the Digest Study", The American Journal of Gastroenterology, vol. 94, No. 10, 1999, pp. 2845-2854.
Woodruff et al., "Cholecystokinin Antagonists", Annu. Rev. Pharmacol. Toxicol. 1991, vol. 31, pp. 469-501.
Remington's 18th Edition, Pharmaceutical Sciences, 1990, pp. 1449-1450.
Noble et al., "International Union of Pharmacology. XXL. Structure, Distribution, and Functions of Cholecystokinin Receptors", Pharmacological Reviews, vol. 51, No. 4, pp. 745-781.
D'Amato et al., "Pulmonary-Allergy, Dermatological, Gastrointestinal & Arthritis: Cholecystokinin-A receptor antagonists: therapies for gastrointestinal disorders", Exp. Opin. Invest. Drugs (1997), 6(7):819-836.
Crawley et al., "Biological Actions of Cholecystokinin", Peptides, vol. 15, No. 4, pp. 731-755, 1994.
Tonini et al., "Progress with Novel Pharmacological Strategies for Gastro-oesophageal Reflux Disease", Drugs 2004; 64(4); 347-361.

(Continued)

*Primary Examiner*—Phyllis G. Spivack
(74) *Attorney, Agent, or Firm*—Sughrue Mion, PLLC

(57) ABSTRACT

Combination of dexloxiglumide and a proton pump inhibitor (PPI) for the treatment of patients suffering from functional dyspepsia and gastroesophageal reflux disease (GERD) is disclosed.

5 Claims, No Drawings

OTHER PUBLICATIONS

Varga, Dexloxiglumide Rotta Research Lab, Investigational Drugs 2002, 3(4):621-626.

Scarpignato et al., Effect of CCK and its antagonists on gastric emptying, J. Physiology (1993), vol. 87, pp. 291-300.

Russo et al., Digestive and Liver Diseases Statistics, 2004, Gastroenterology 2004; vol. 126, pp. 1448-1453.

Dent et al., "Sympton evaluation in reflux disease: workshop background, processes, terminology, recommendations, and discussion outputs", Gut 2004; vol. 53, pp. 1-24.

* cited by examiner

DELOXIGLUMIDE AND PROTON PUMP INHIBITOR COMBINATION IN THE TREATMENT OF GASTROINTESTINAL DISORDERS

FIELD OF THE INVENTION

The present invention relates to cholecystokinin-1 (CCK1) receptor antagonists and the combination of CCK1 receptor antagonists and proton pump inhibitors (PPI) for the treatment of patients suffering from gastrointestinal or related disorders that have failed to completely respond to conventional acid suppression therapy.

BACKGROUND OF THE INVENTION

Physicians have long recognized that conditions affecting the upper gastrointestinal (GI) tract commonly produce upper abdominal pain, discomfort, abdominal fullness, bloating, early satiety, nausea, heartburn and regurgitation. Such symptoms are typically postprandial and occur either alone or in combination. Overall, upper GI symptoms, including both dyspeptic-type and reflux-type, affect more than 25% of adults in the Western world and have a significant, negative impact on both functional status and sense of individual well-being (Tougas et al., Am J Gastroenterol. 1999; 94: 2845-2854). Symptoms related to disorders of upper gut function are among the most common, presenting complaints in primary-care and GI specialty medical practice. These disorders commonly include GERD (gastroesophageal reflux disease), GERD with erosion, NERD (nonerosive reflux disease), PUD (peptic ulcer disease), FD (functional dyspepsia also indicated as nonulcer dyspepsia), diabetic gastroparesis, gastrointestinal ulcers, Zollinger-Ellison syndrome, and antral G-cell hyperplasia.

Conventional acid suppression therapy includes the use of antacid agents, pepsin inhibitors, gastric mucosa protective agents, anticholine agents for suppressing the secretion of gastric hydrochloric acid, parasympathetic blocking agents, histamine H2 receptor antagonists (hereinafter referred to as "H2 blockers"), proton pump inhibitors, etc. Examples of proton pump inhibitors include Lansoprazole (brand names: Prevacid®, Zoton®, U.S. Pat. No. 4,628,098), Omeprazole (brand names: Losec®, Prilosec®, U.S. Pat. Nos. 4,255,431 and 5,693,818), Pantoprazole (brand names: Protonix®, Somac®, U.S. Pat. No. 4,758,579), Rabeprazole (brand names: Aciphex®, Pariet®, U.S. Pat. No. 5,045,552) and AZD-0865 (Holstein et al., Gastroenterology 2004, 126 (4, Suppl 2): Abst M1436).

Proton pump inhibitors (PPIs) reduce gastric acid secretion by inhibition of the gastric proton pump in parietal cells. However, PPIs and other conventional treatments that reduce gastric acidity do not adequately address all patients. For example, esophagitis may be reduced using proton pump inhibitors, but endoscopy in patients with predominantly reflux-type symptoms reveals that esophagitis may still exist in a minority of patients.

Moreover, patients with predominantly dyspeptic-type symptoms often have no identifiable gross or microscopic lesions in either the esophagus or stomach. Although an anatomic lesion is typically absent in dyspeptic patients, a variety of other abnormalities (e.g., in gastric accommodation, antral motility/emptying and antroduodenal coordination) have been identified and considered to be pathophysiologic, but none is found consistently in all patients. Likewise, attempts to establish an etiologic association between the presence of gastric acid and dyspeptic symptoms has been unsuccessful, even when ambulatory pH monitoring has been employed. Hence, there is no unifying mechanism underlying the generation of symptoms collectively termed "dyspeptic," including upper abdominal/epigastric pain and discomfort, abdominal fullness, bloating, belching/eructation, early satiety, nausea and/or vomiting.

Upper GI disorders are typically classified by anatomic region, e.g., those of esophageal origin and those of gastroduodenal origin, based on epidemiological evidence pointing to the existence of site-specific clusters of symptoms. However, the GI tract's anatomic continuity and integrated function in digestion and absorption of nutrients makes the separation of symptom clusters by site somewhat artificial. In fact, considering the diaphragm to be an anatomic boundary for defining upper GI disorders, e.g., attributing symptoms localized above the diaphragm such as heartburn to the esophagus, a thoracic organ, and symptoms localized below the diaphragm such as epigastric pain and discomfort to the stomach, an abdominal organ, is not very useful. For example, "heartburn" as the sole or predominant symptom to define gastroesophageal reflux disease (GERD) has very low sensitivity (38%) albeit high specificity (about 90%) (Dent et al., Gut. 2004, 53(May):Supp 4:1-24). Rather than occurring alone as a manifestation of GERD, heartburn is associated with epigastric pain in at least two thirds of patients.

A study comparing the treatment strategies of 500 patients with dyspeptic symptoms (pain or discomfort in the epigastrium with or without heartburn, regurgitation, nausea, vomiting or bloating) shows the difficulty in assessing patients (*H. pylori* test-and eradicate versus prompt endoscopy) (Lassen et al, Lancet 2000, 356:455-460). Although the main entry criterion was epigastric pain or discomfort, which was reported by all patients, 32% had heartburn and/or regurgitation as their dominant symptom, which was almost as many patients as had dominant epigastric pain (37%). (See Lassen et al.) Therefore, the available data indicate that significant overlap of symptoms exists in esophageal and gastric disorders; GERD patients have dyspeptic symptoms and dyspeptic patients have heartburn and/or regurgitation.

It is estimated that 15-19% of the American population experience symptoms of GERD at least weekly and 10% or more experience associated dyspeptic symptoms. (Locke et al., Gastroenterology 1997, 112 (5):1448-1456) Based on results from the National Ambulatory Medical Care Survey, heartburn and indigestion (dyspepsia) together were estimated to account for over 1.8 million outpatient clinic visits in the United States during the year 2000 (Russo et al, Gastroenterology 2004, 126:1448-1453).

Cholecystokinin (CCK) belongs to the group of substances known as brain-gut peptides and function as a neuropeptide and as a gut hormone. (Noble et al., Pharmacol. Rev. 1999, 51(4):745-781; Crawley et al., Peptides 1994, 15(4):731-755). It is now evident that at least two different receptors, namely CCK1 (formerly CCKA or alimentary) and CCK2 (formerly CCKB or brain) receptors, mediate CCK biological actions. (Noble et al., Pharmacol. Rev., 1999, 51(4):745-781; Woodruff and Hughes, Ann. Rev. Pharmacol. 1991, 31:469-501). CCK1 receptors are found in peripheral tissues, including the GI tract.

CCK is secreted primarily in response to meals and plays a well-recognized role in regulating gallbladder contraction and pancreatic enzyme secretion. Over the last decade, considerable evidence has emerged to support the concept that CCK plays an equally important role in the regulation of motor and sensory functions at various levels of the human upper GI tract. Specifically, the native peptide delays gastric emptying, modulates gastric sensory function (especially in response to fat), increases the rate of meal-induced, transient lower esophageal sphincter relaxations (TLESRs) and affects small bowel and colonic transit.

The CCK1 antagonists loxiglumide and dexloxiglumide have demonstrated the ability to reverse the physiologic effects of CCK on gastric emptying and to decrease dyspeptic symptoms induced by air distension and fat infusion. By example, loxiglumide reduced both exogenous and endogenous CCK-induced delay in gastric emptying of liquids and solids in healthy subjects (Borovicka et al., Am J Physiol. 1996, 271:448-453; Schwizer et al., Gut. 1997, 41(4):500-504). Dexloxiglumide reversed the diminished tolerance to water volume that occurred from CCK release in response to duodenal lipid infusion; the effect was due to reduction of intragastric volume, primarily due to accelerated gastric emptying (Lal et al., Am J Physiol Gastrointest Liver Physiol. 2004, 287(1):72-79). When proximal gastric relaxation was produced in healthy subjects by duodenal infusion of lipid, a potent stimulus of CCK release, the relaxation was reversed by loxiglumide (Feinle et al., Gastroenterology 1996, 110(5): 1379-1385). Also, loxiglumide modulated antro-pyloroduodenal dysmotility, which is postulated to play a role in generation of dyspeptic symptoms, after it was experimentally induced in healthy subjects by intraduodenal infusion of a mixed liquid meal (Katschinski et al., Eur J Clin Invest. 1996, 26(7):574-583). Loxiglumide was also able to reverse the lowering of intragastric pressure of healthy subjects after duodenal infusion of lipids induced sensations such as fullness and nausea (See Feinle et al., 1996).

In patients with nonulcer dyspepsia and delayed gastric emptying, loxiglumide was shown to accelerate gastric emptying by comparison to placebo (Chua AS, Bekkering M, et al., 1994). Loxiglumide significantly improved dyspeptic symptoms in patients with non-ulcer dyspepsia in an 8-week study (Chua et al., Ann NY Acad. Sci. 1994, 713:298-299). In another study in patients with functional dyspepsia, aggravation of nausea, fullness, discomfort, bloating and pain was produced by duodenal infusion of lipid with or without balloon distension; dexloxiglumide significantly improved dyspepsia symptom scores compared to placebo (Feinle et al., Gut. 2001, 48(3): 347-355).

Pharmaceutical compositions comprising CCKB antagonists and a proton pump inhibitor to control gastric acid secretion in gastrointestinal disorders have been described in the literature. (See WO 04/098610, WO 04/101533, WO 04/098609, WO 03/041714, WO 01/90078, WO 01/85724, WO 01/85723, WO 01/85704, WO 01/85167, and WO 93/12817) CCK-B receptors mediate CCK biological actions in the brain and are one of several regulators of gastric acid secretion. It is the CCK1 receptors, however, that mediate the CCK biological actions in peripheral tissues including gastric emptying and esophageal sphincter effects.

In addition, combination therapy of a PPI and a second agent, e.g., loxiglumide, to improve impaired esophageal motility has been disclosed as a possible treatment to gastroesophageal reflux disease. (Tonini et al., Drugs 2004, 64(4): 347-361). International Application Nos. PCT/EP2004/050936 and PCT/EP2005/050336 also disclose pharmaceutical combinations of a proton pump inhibitor and a compound that modifies gastrointestinal motility. Both international applications disclose that dexloxiglumide may be useful for therapy of irritable bowel syndrome (IBS) or GERD and may be used to modify gastrointestinal motility.

However, there is no approved treatment for dyspeptic symptoms associated with gastrointestinal disorders. In addition, there is no convincing evidence that current GI treatments successfully relieve dyspeptic symptoms. While there is compelling evidence for the effectiveness of acid suppression therapy in patients with symptomatic heartburn and/or regurgitation due to GERD, there is a lack of convincing evidence of the effectiveness of acid suppression therapy for dyspeptic symptoms associated with GERD. Indeed, it is a frequent observation that the majority of patients treated with a PPI for GERD symptoms are left with residual dyspeptic symptoms.

Since current acid suppression treatment options for gastrointestinal disorders with dyspepsia type symptoms do not adequately address the complexities of these diseases, there remains a need for a treatment that is effective in at least a substantial portion of this patient population, without producing severe adverse effects.

SUMMARY OF THE INVENTION

The present invention relates to cholecystokinin-1 (CCK1) receptor antagonists and the combination of CCK1 receptor antagonists and proton pump inhibitors (PPI) for the treatment of patients suffering from gastrointestinal or related disorders that have failed to completely respond to conventional acid suppression therapy. The present invention describes for the first time that the clinical administration of a CCK1 antagonist is effective for the treatment of patients suffering from gastrointestinal or related disorders whom have failed to completely respond to conventional acid suppression therapy. Moreover, these patients may demonstrate unexpected improvement in residual dyspeptic-type symptoms.

In one embodiment, the invention relates to a method of treating gastrointestinal disorders comprising administering to a patient failing to completely respond to conventional acid suppression therapy a CCK1 receptor antagonist in an amount effective to treat the gastrointestinal disorder. For example, the subjects being treated may not be completely responsive to conventional acid suppression therapy and are suffering from GERD (Gastroesophageal Reflux Disease), GERD with erosion, NERD (NonErosive Reflux Disease), PUD (Peptic Ulcer Disease), FD (Functional Dyspepsia), Diabetic Gastroparesis, Nocturnal heartburn, Heartburn, Bloating, gastrointestinal ulcers, Zollinger-Ellison syndrome and antral G-cell hyperplasia.

In another embodiment, the invention relates to pharmaceutical compositions for treating gastrointestinal disorders of patients failing to completely respond to conventional acid suppression therapy comprising: (i) a CCK1 receptor antagonist; and (ii) a pharmaceutically acceptable carrier or excipient, wherein the CCK1 receptor antagonist is present at a therapeutically effective dosage.

In another embodiment, the invention relates to a method of treating a gastrointestinal disorder comprising administering to a patient in need of such treatment a first amount of a CCK1 receptor antagonist and a second amount of a proton pump inhibitor (PPI), the first and second amounts in combination being effective at improving at least one symptom from the gastrointestinal disorder.

In another embodiment, the invention relates to pharmaceutical compositions for treatment of gastrointestinal disorders comprising: (i) a CCK1 receptor antagonist; (ii) a proton pump inhibitor (PPI); and (iii) a pharmaceutically acceptable carrier or excipient, wherein the CCK1 receptor antagonist is present at a therapeutically effective dosage.

DETAILED DESCRIPTION OF THE INVENTION

The present invention relates to cholecystokinin-1 (CCK1) receptor antagonists and the combination of CCK1 receptor antagonists and proton pump inhibitors (PPI) for the treatment of patients suffering from gastrointestinal or related disorders that have failed to completely respond to conventional acid suppression therapy. Preferably, the CCK1 receptor antagonist and proton pump inhibitor are administered at therapeutically effective dosages which, when combined, provide a beneficial effect.

At least ten classes of CCK1 receptor antagonists are now available (D'Amato et al., Exp. Opin. Invest. Drugs 1997, 6(7):819-836). The amino acid derivative CCK receptor antagonist proglumide was discovered more than 20 years ago by Rotta Research Laboratorium SpA. However, it has low potency and specificity (the compound also effectively binds CCK2 receptors). More recently synthesized glutaramic acid derivatives, lorglumide and loxiglumide (both from Rotta Research Laboratorium SpA), are potent, specific competitive antagonists of CCK1 receptors. They are active after oral administration and are able to antagonize the effects of both endogenous and exogenous CCK. These selective CCK1 receptor antagonists are effective in increasing GI motility.

Dexioxiglumide (R-4-(3,4-dichlorobenzoylamino)-5-(N-3-methoxypropyl-pentylamino)-5-oxo-pentanoic acid), the (R)-isomer of loxiglumide, is approximately twice as potent as the racemic compound, because the anti-CCK activity resides in the (R)-form (see D'Amato et al., 1997). Dexloxiglumide has been developed by Rotta Research Laboratorium SpA for the treatment of diseases in which CCK1 receptor activity is potentially involved, including gastrointestinal motility, food intake and pancreatic disorders (Varga et al., Curr. Opin. Investig. Drugs 2002, 3(4):621-626). Results from both preclinical and clinical studies indicate that dexloxiglumide is an effective inhibitor of gallbladder contraction, improves lower esophageal sphincter (LES) function, accelerates gastric emptying, and accelerates colonic transit, and therefore has potential as an effective treatment for gastrointestinal and related disorders (Scarpignato et al., J. Physiol. Paris 1993, 87(5):291-300; See D'Amato et al., 1997; Feinie et al., Gut 2001, 48(3):347-355).

Definitions

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy."

"Alkoxy" means an alkyl-O— group; non-limiting examples of suitable alkoxy groups include methoxy, ethoxy, n-propoxy, isopropoxy and butoxy. The alkyl group is linked to an adjacent moiety through the ether oxygen.

The compounds of Formula I can be administered as racemic mixtures or enantiomerically pure compounds within the scope of the present invention.

The compounds of Formula I can form salts and solvates that are also within the scope of this invention.

"Solvate" means a physical association of a compound of this invention with one or more solvent molecules. This physical association involves varying degrees of ionic and hydrogen bonding. Solvates of the compounds of the invention are also contemplated as within the scope of the present invention. Reference to a compound of Formula I herein is understood to include reference to salts and solvates thereof, unless otherwise indicated.

Within the meaning of the present invention, the term "visceral" is used in its broadest sense to refer to organs that are located in the trunk of the body, e.g., the heart, liver, intestines.

The terms "gut motility", "gastric motility", "GI motility", and "intestinal motility" are used interchangeably to refer generally to the peristaltic movements of the gastrointestinal tract. These terms are also used more specifically to refer to contractions of the smooth muscle of the intestine, which result in propelling intestinal contents through the gut (the process termed "peristalsis").

The term "combination" applied to active ingredients is used herein to define a single pharmaceutical composition (formulation) comprising both drugs of the invention (i.e., a CCK1 receptor antagonist and a proton pump inhibitor) or two separate pharmaceutical compositions (formulations), each comprising a single drug of the invention (i.e., a CCK1 receptor antagonist or a proton pump inhibitor) and are administered conjointly.

Within the meaning of the present invention, "administered conjointly" is used to refer to administration of a CCK1 receptor antagonist and proton pump inhibitor simultaneously in one composition, or simultaneously in different compositions, or sequentially. For the sequential administration to be considered "conjoint," the CCK1 receptor antagonist and proton pump inhibitor must be administered separated by a time interval that permits the resultant beneficial effect for treating, preventing, arresting, delaying the onset of and/or reducing the risk of developing in a mammal a gut motility disorder associated with gastrointestinal or related disorders. For example, within the meaning of the present invention the CCK1 receptor antagonist and proton pump inhibitor may be administered on the same day (e.g., each—once or twice daily), preferably within an hour of each other, and most preferably simultaneously.

The term "treating" is used herein to mean to relieve, alleviate, delay, reduce or prevent at least one symptom of a disease in a subject. For example, in relation to a gastrointestinal disorder, the term "treat" may mean to relieve or alleviate at least one symptom that includes, but is not limited to, increased tension on the wall of the stomach, increased intravisceral pressure, cramps, colitis, gnawing, abdominal pain, constipation, diarrhea, nausea, vomiting, urge to defecate, tenesmus, hematochezia, etc. Within the meaning of the present invention, the term "treat" also means to arrest, delay the onset (i.e., the period prior to clinical manifestation of a disease) and/or reduce the risk of developing or worsening a disease.

For example, as disclosed herein, a prophylactic administration of a CCK1 receptor antagonist in combination with a proton pump inhibitor can protect a recipient subject at risk of developing a gastrointestinal disorder. Similarly, according to the present invention, a therapeutic administration of a CCK1 receptor antagonist conjointly with a proton pump inhibitor can lead to slow-down in the development of clinical symptoms or even regression of symptoms.

Within the meaning of the present invention, the term "proton pump inhibitor" is used to refer to compounds that can suppress the function of the hydrogen-potassium adenosine triphosphatase enzyme system to reduce the release of acid in the stomach and intestines. Inhibitors of $H^+$-$K^+$ ATPase (proton pump) can bind irreversibly or reversibly to the enzyme. Agents referred to as Proton Pump Inhibitors (PPIs) typically include irreversible inhibitors. The most commonly known irreversible proton pump inhibitors include: Omeprazole (brand names: Losec®, Prilosec®), Lansoprazole (brand names: Prevacid®, Zoton®), Esomeprazole (brand names:

Nexium®), Pantoprazole (brand names: Protonix®, Somac®) and Rabeprazole (brand names: Aciphex®, Pariet®). These irreversible PPIs contain a sulfinyl group situated between the benzoimidazole and pyridine rings. Though, at neutral pH, omeprazole, lansoprazole, rabeprazole and pantoprazole are chemically stable, lipid soluble and devoid of inhibitory activity, at acidic pH these compounds rearrange to form a sulfenic acid and a sulfenamide. These formed species are capable to interact with sulfhydryl groups of the enzyme and provide irreversible inhibition.

Reversible inhibitors are also referred to as Acid Pump Antagonists (APAs). APAs differ from the classical PPIs listed above in the way they inhibit $H^+$-$K^+$ ATPase. For example, acid induced transformation is not necessary for activation and enzyme kinetics typically shows reversible binding to the enzyme for APAs. Examples of suitable APAs include, but are not limited to, CS-526 (Sankyo), AZD0865 (Astra Zeneca), Soraprazan (Altana AG); other APAs are described by Sachs et al. U.S. Pat. No. 6,132,768, the disclosure of which is hereby incorporated by reference in its entirety.

Accordingly, within the meaning of the present invention, the term "proton pump inhibitor" includes all the compounds that can suppress $H^+$-$K^+$ ATPase activity acting either as irreversible or reversible inhibitors.

The terms "cholecystokinin-1 (CCK1) receptor antagonist" or "CCK1 receptor antagonist drugs" are used to refer to compounds that can suppress the normal function of CCK1 receptor, such as referred CCK1 receptor antagonist drugs of the invention are derivatives of glutamic acid, most preferably derivatives of (R) 5-pentylamino-5-oxopentanoic acid, such as Dexloxiglumide.

The CCK1 receptor antagonists of the present invention are glutamic acid derivatives, namely 5-pentylamino-5-oxopentanoic acid derivatives. These derivatives and methods for their preparation are disclosed in U.S. Pat. Nos. 4,769,389, 4,880,938 and 5,130,474, the disclosures of which are hereby incorporated by reference in their entirety. The glutamic acid derivatives of the present invention can be represented by the general formula (I):

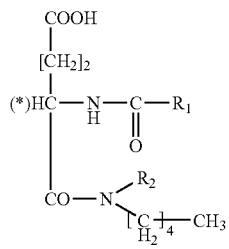

I wherein:
$R^1$ is selected from the group consisting of 2-naphthyl, 3,4-dichlorophenyl and 3,4-dimethylphenyl;
$R^2$ is a pentyl group or an alkoxyalkyl group with 4 carbon atoms;

and pharmaceutically acceptable salts thereof.

The compounds of the present invention include enantiomers, hydrates and mixtures of the compounds of Formula (I). For example, the substituents on the chiral center, marked with an asterisk in formula (I), may have the R (rectus) or R,S (Rectus, Sinister) conformation. Preferably, the substituents on the central chiral group have the R (rectus) conformation.

Exemplary CCK1 receptor antagonists according to the present invention include, but are not limited to:
Dexloxiglumide (R-4-(3,4-dichlorobenzoylamino)-5-(N-3-methoxypropyl-pentylamino)-5-oxo-pentanoic acid);
Loxiglumide (R,S-4-(3,4-dichlorobenzoylamino)-5-(N-3-methoxypropyl-pentylamino)-5-oxo-pentanoic acid);
Lorglumide (R,S-4-[(3,4-Dichlorobenzoyl)amino]-5-(dipentylamino)-5-oxopentanoic acid);
Amiglumide ((R)-4-(2-Naphthamido)-N,N-dipentylglutaramic acid);

as well as polymorphs, solvates, pharmaceutically acceptable salts, and mixtures thereof.

Various salts and isomers (including stereoisomers and enantiomers) of the drugs listed herein can be used. The nature of the salt or isomer is not critical, provided that it is non-toxic and does not substantially interfere with the desired pharmacological activity.

For example, pharmaceutically acceptable base addition salts are formed with metals or amines, such as alkali and alkaline earth metals or organic amines. Examples of metals that may be used as cations include sodium, potassium, magnesium, calcium, and the like. Examples of suitable amines include N,N'-dibenzylethylenediamine, choline, diethanolamine, dicyclohexylamine, ethylenediamine and N-methylglucamine.

As used herein the term "therapeutically effective" applied to dose or amount refers to that quantity of a compound or pharmaceutical composition that is sufficient to result in a desired activity upon administration to a mammal in need thereof. More specifically, the term "therapeutically effective" refers to that quantity of a compound or pharmaceutical composition that is sufficient to reduce or eliminate at least one symptom of a gastrointestinal disorder.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" applied to pharmaceutical compositions of the invention refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical excipients also include binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch, sodium starch glycolate, crosslinked carboxymethyl cellulose sodium or crosslinked povidone); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. For other examples see "Remington's Pharmaceutical Sciences" by E.W. Martin, 18th Edition, the disclosure of which is hereby incorporated by reference in its entirety.

The active agents of the present invention may be administered orally, topically, parenterally, or mucosally (e.g., buccally or rectally) in dosage unit formulations containing conventional non-toxic pharmaceutically acceptable carriers. In preferred embodiments, the active agents of the present invention may be administered orally. For example, the active agents may be administered orally in the form of a capsule or a tablet (see Remington's Pharmaceutical Sciences, Mack 5 Publishing Co., Easton, Pa.). The orally administered medicaments may be administered in the form of a modified release formulation or device, including diffusion-controlled systems, osmotic devices, dissolution-controlled matrices, and erodible/degradable matrices.

For oral administration in the form of a tablet or capsule, the active drug component can be combined with a non-toxic, pharmaceutically acceptable excipients such as binding agents, fillers, lubricants, disintegrants, coloring and flavoring agents, gelatin, sweeteners, natural and synthetic gums, buffer salts, carboxymethylcellulose, polyethyleneglycol and waxes. For oral administration in liquid form, the drug components can be combined with non-toxic, pharmaceutically acceptable inert carriers, suspending agents, emulsifying agents, non-aqueous vehicles and preservatives. Stabilizing agents such as antioxidants (e.g., BHA, BHT, propyl gallate, sodium ascorbate, and citric acid) can also be added to stabilize the dosage forms.

For liquid preparations the oral administration can take the form of, for example, solutions, syrups, emulsions or suspensions, or they can be presented as a dry product for reconstitution with water or other suitable vehicle before use. Preparations for oral administration can be suitably formulated to give controlled or postponed release of the active compound.

The active drugs can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines, as is well known.

Active drugs may also be coupled with soluble polymers as targetable drug carriers. Such polymers can include polyvinyl-pyrrolidone, pyran copolymer, polyhydroxy-propyl methacrylamide-phenol, polyhydroxy-ethyl-aspartamide-phenol, or polyethyleneoxide-polylysine substituted with palmitoyl residues.

Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

The formulations of the invention can be delivered parenterally, e.g., by intravenous (i.v.), subcutaneous (s.c.), intramuscular (i.m.), subdermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative. The compositions can take such forms as excipients, suspensions, solutions, or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use.

As disclosed herein, a proton pump inhibitor and CCK1 receptor antagonist can be mixed with excipients that are pharmaceutically acceptable and compatible with the active ingredients. In addition, if desired, the preparations may also include minor amounts of auxiliary substances such as wetting or emulsifying agents, pH buffering agents, and/or agents that enhance the effectiveness of the pharmaceutical composition.

Although the active agents of the present invention may be administered in divided doses, for example, two or three times daily, a single daily dose is preferred, with a single daily dose of both agents in one composition or in two separate compositions administered simultaneously being most preferred.

The instant invention also encompasses a process for preparing pharmaceutical compositions comprising combining a CCK1 receptor antagonist and/or a proton pump inhibitor with a pharmaceutically acceptable carrier and/or excipient.

Preferred specific amounts of the proton pump inhibitor that may be used in unit dosage amounts of the invention include, for example, about 1 to 60 mg, preferably about 5 to 50 mg and more preferably about 10 to 40 mg. Preferred specific amounts of the CCK1 receptor antagonist which may be used in unit dosage amounts of the invention include, for example, about 10 to 1000 mg, preferably about 50 to 600 mg and more preferably about 100 to 400 mg.

The invention also provides a pharmaceutical pack or kit comprising one or more containers containing one or more of the ingredients of the formulations of the invention. In a related embodiment, the present invention provides a kit for the preparation of the pharmaceutical compositions of the invention, said kit comprising a CCK1 receptor antagonist in a first container, and a proton pump inhibitor in a second container, and, optionally, instructions for admixing the two drugs and/or for administration of the compositions. Each container of the kit may also optionally include one or more physiologically acceptable carriers and/or excipients and/or auxiliary substances. Associated with such container(s) can be a notice in the form prescribed by a governmental agency regulating the manufacture, use or sale of pharmaceuticals or biological products, which notice reflects approval by the agency of manufacture, use or sale for human administration.

The compositions may, if desired, be presented in a pack or dispenser device that may contain one or more unit dosage forms containing the active ingredient. The pack may, for example, comprise metal or plastic foil, such as a blister pack. The pack or dispenser device may be accompanied by instructions for administration. Compositions of the invention formulated in a compatible pharmaceutical carrier may also be prepared, placed in an appropriate container, and labeled for treatment of an indicated condition.

The compositions of the invention may be administered in a modified release formulation. Modified release dosage forms provide a means for improving patient compliance and for ensuring effective and safe therapy by reducing the incidence of adverse drug reactions. Compared to immediate release dosage forms, modified release dosage forms can be used to prolong pharmacological action after administration, and to reduce variability in the plasma concentration of a drug throughout the dosage interval, thereby eliminating or reducing sharp peaks.

The majority of modified release dosage forms comprise a core either coated with or containing a drug. The core may be coated with a release-modifying polymer within which the drug is dispersed. The release-modifying polymer may then disintegrate gradually, releasing the drug over time. Thus, the outer-most layer of the composition effectively slows down and thereby regulates the diffusion of the drug across the coating layer when the composition is exposed to an aqueous environment, i.e. the gastrointestinal tract. The net rate of diffusion of the drug is mainly dependent on the ability of the gastric fluid to penetrate the coating layer or matrix and on the solubility of the drug itself.

According to the methods of the present invention, the pharmaceutical compositions are administered to a patient at therapeutically effective doses, preferably, with minimal toxicity. Preferably, the proton pump inhibitor and the CCK1 receptor antagonist are each used at a dosage which, when combined, provide an enhanced effect, most preferably, an effect not observed upon administration of each agent alone.

The efficacy of a CCK1 receptor antagonist or PPI was determined in preclinical studies using small animal models (e.g., rats) in which both the CCK1 receptor antagonist and proton pump inhibitor have been found to be therapeutically effective and in which these drugs can be administered by the same route proposed for the human clinical trials.

For any pharmaceutical composition used in the methods of the invention, the therapeutically effective dose can be estimated initially from animal models to achieve a circulating plasma concentration range that includes the IC50 (i.e., the concentration of the test compound which achieves a half-maximal inhibition). Dose-response curves derived from animal systems may then be used to determine testing doses for the initial clinical studies in humans. In safety determinations for each composition, the dose and frequency of administration should meet or exceed those anticipated for use in the clinical trial.

As disclosed herein, the dose of the CCK1 receptor antagonist in the compositions of the present invention is determined to ensure that the dose administered continuously or intermittently will not exceed an amount determined after consideration of the results in test animals and the individual conditions of a patient. A specific dose naturally varies (and is ultimately decided according to the judgment of the practitioner and each patient's circumstances) depending on the dosage procedure, the conditions of a patient or a subject animal such as age, body weight, sex, sensitivity, feed, dosage period, drugs used in combination, seriousness of the disease, etc. For example, an appropriate dose of a CCK1 receptor antagonist is generally in the range of about 1 to about 20 mg per kg of the body weight.

Toxicity and therapeutic efficacy of the compositions of the invention may be determined by standard pharmaceutical procedures in experimental animals, e.g., by determining the LD50 (the dose lethal to 50% of the population) and the ED50 (the dose therapeutically effective in 50% of the population). The dose ratio between therapeutic and toxic effects is the therapeutic index and can be expressed as the ratio ED50/LD50. Compositions that exhibit large therapeutic indices are preferred.

The data obtained from animal studies may be used in formulating a range of doses for use in humans. The doses of derivatives used in humans are preferably within a range of circulating concentrations that include the ED50 with little or no toxicity. The dosage can vary within this range depending upon the dosage form employed and the route of administration utilized.

The drug combinations of the invention are not only highly effective at relatively low doses but also possess low toxicity and produce few side effects. Indeed, the most common side effect resulting from the use of a CCK1 receptor antagonist and a proton pump are mild and transient nausea, diarrhea, abdominal pain, malaise, and increased appetite.

The following examples are merely illustrative of the present invention and should not be construed as limiting the scope of the invention in any way as many variations and equivalents that are encompassed by the present invention will become apparent to those skilled in the art upon reading the present disclosure.

Preclinical Studies

Effect on Acute Reflux Esophagitis in Rats

Male rats of 175-200 g body weight were fasted for 24 hours prior the experiment. Water was allowed ad libitum. Under ether anesthesia, the abdomen was incised along the midline, and both pylorus and limiting ridge (transitional region between the forestomach and corpus) were simultaneously ligated. Consequently, the total capacity of the stomach to hold gastric juice was greatly diminished, resulting in reflux of gastric juice into the esophagus. Following ligation of pylorus and limiting ridge, the test compounds were given intraduodenally (5 ml/kg), and the abdomen was closed by suturing. After 3 hours, rats were killed by ether overdose and the gastroesophageal portion was excised. The lesion in the thoracic esophagus was scored macroscopically, using a lesion index according to the following criteria: no lesion as 0; edema as 1; reddening as 2; the length of hemorrhagic area<20 mm as 3; the length of hemorrhagic area 20-30 mm as 4; the length of hemorrhagic area 30-40 mm as 5; the length of hemorrhagic area>40 mm or perforation as 6.

The doses of the tested compounds which reduce of 50% the esophagus lesions ($ED_{50}$) and their P=0.05 fiducial limits were calculated from the dose-response regression line. The results obtained are provided in Table 1.

TABLE 1

Protective effects of dexloxiglumide, omeprazole and their combination treatment on acute reflux esophagitis in pylorus-ligated rats

| Treatment Group | Doses (mg/kg) | Average Score lesions | % Effect vs. control | $ED_{50}$ |
|---|---|---|---|---|
| Control | Saline | 5.8 | — | — |
| Dexloxiglumide | 10 | 5.8 | 0 | 37.5 mg/kg |
|  | 20 | 4.8 | 17.2 |  |
|  | 40 | 2.6 | 51.7 |  |
|  | 60 | 2.2 | 62.1 |  |
|  | 100 | 0 | 100 |  |

TABLE 1-continued

Protective effects of dexloxiglumide, omeprazole and their combination
treatment on acute reflux esophagitis in pylorus-ligated rats

| Treatment Group | Doses (mg/kg) | Average Score lesions | % Effect vs. control | $ED_{50}$ |
|---|---|---|---|---|
| Omeprazole | 0.1 | 5.6 | 3.4 | 5.4 mg/kg |
|  | 0.3 | 5.8 | 0 |  |
|  | 1.0 | 4.8 | 14.3 |  |
|  | 3.0 | 2.7 | 53.4 |  |
| Control | Saline | 5.9 | — |  |
| Dexloxi + Omeprazole | 10 + 0.3 | 3.8 | 35.6 | (CR2017 + 0.3 mg/kg |
| " | 10 + 1.0 | 3.0 | 49.2 | Omeprazole) = 14.4 mg/kg |
| " | 20 + 0.3 | 2.1 | 64.4 | (CR2017 + 1.0 mg/kg |
| " | 20 + 1.0 | 1.2 | 79.7 | Omeprazole) = 9.8 mg/kg |
| " | 40 + 0.3 | 1.2 | 79.7 |  |
| " | 40 + 1.0 | 0 | 100 |  |

The calculated protective effects of Dexloxiglumide and Omeprazole administered separately were 37.5 mg/kg and 5.4 mg/kg, respectively. The combination treatment of the two compounds produced an increase of protective effect. The calculated $ED_{50}$ for the combination treatment were 14.4 mg/kg for dexloxiglumide plus omeprazole (0.3 mg/kg) and 9.8 mg/kg for dexloxiglumide plus omeprazole (1 mg/kg), respectively.

On average the combination treatment produced a synergistic increase in efficacy for both examined drugs. For example, the combination treatment of 20 mg/kg dexloxiglumide plus 1 mg/kg omeprazole produced an 80% protective effect versus a 32% expected, this latter being the sum of the results obtained with the equivalent separate experiments, i.e., 17.2 and 14.3% of protective effect.

Clinical Studies

Safety and efficacy of Dexloxiglumide in the Relief of Dyspeptic Symptoms

To assess the safety and efficacy of dexloxiglumide in the relief of dyspeptic symptoms, we propose to conduct a placebo-controlled, double-blind study in male and female patients who have a documented history of functional dyspesia (FD) and received an adequate dose of a PPI for at least 4 weeks within the preceding 12 months. Only patients who continue to experience symptoms of FD while on an adequate course of treatment with a proton pump inhibitor (PPI) will be eligible for enrollment. The synopsis below describes the study in further detail.

An 8-week treatment, prospective, randomized, double-blind, placebo-controlled, single-dose, parallel group, multicenter study will be performed to investigate the safety and efficacy of dexloxiglumide 300 mg b.i.d. for the relief of dyspeptic symptoms in patients being treated with proton pump inhibitors.

A total of 200 male and female patients (100 per treatment group), 18 years of age or older, will be enrolled in this 8-week treatment, prospective, randomized, double-blind, placebo-controlled, parallel group study. To participate, patients must have received an adequate dose of a PPI for ≧4 weeks during the previous 12 months without adequate relief of dyspeptic symtoms and have no endoscopic evidence of esophageal or gastric mucosal pathology on esophagogastroduodenoscopy (EGD) and must have FD symptoms (pain/discomfort centered in the upper abdomen, early satiety, fullness, bloating in the upper abdomen, nausea, vomiting or retching and belching or burping) present for ≧6 months. Upon entry into the run-in period, all patients will have their acid-suppression therapy standardized to esomeprazole 40 mg PO once daily (q.d.) and will continue on this regimen throughout the 4- to 6-week run-in and 8-week double-blind treatment periods.

Patients will first enter a 4- to 6—week, run-in period, during which they will use an electronic diary to report the frequency and severity of their dyspeptic symptoms as well as heartburn, regurgitation, nighttime heartburn and nighttime regurgitation. In order to assure that dyspeptic/FD symptoms predominate over heartburn symptoms (if present despite PPI treatment) heartburn and acid regurgitation will also be assessed daily during the two-week run-in period. Delineation of the patient's occasional heartburn symptoms at baseline will also allow assessment of the potential efficacy of dexloxiglumide for the relief of these symptoms remaining despite adequate PPI therapy. To be eligible for randomization, patients reporting heartburn and regurgitation during the run-in period must demonstrate that their heartburn and regurgitation are of lesser severity and frequency than their dyspeptic symptoms.

At the end of the run-in period, patients meeting pre-specified dyspeptic symptom frequency and severity criteria (i.e., at least two dyspeptic symptoms rated "relevant" or "severe" for at least two days of each week) will be randomized 1:1 to receive dexloxiglumide for 8 weeks at a dose of 300 mg b.i.d. or placebo. Thus, the safety and efficacy of dexloxiglumide in the relief of dyspeptic symptoms and, more particularly, functional dyspesia (FD) will be evaluated.

While the invention has been depicted and described with reference to exemplary embodiments, such reference does not imply a limitation on the invention, and no such limitation is to be inferred. The invention is capable of considerable modification, alteration, and equivalents in form and function, as will be apparent to those of ordinary skill in the pertinent art having the benefit of this disclosure. Consequently, the invention is intended to be limited only by the spirit and scope of the appended claims, giving full cognizance to equivalence in all respects. All references cited herein are hereby incorporated by reference in their entirety.

What is claimed is:

1. A method of treating a gastrointestinal disorder, comprising administering a first dosage amount of from 100 to 1000 mg of dexloxiglumide and a second dosage amount of from 5 to 40 mg of a proton pump inhibitor, said first and second amounts in combination being effective for treating patients suffering from functional dyspepsia or gastroesophageal reflux disease.

2. The method of claim 1, wherein the dexloxiglumide and the proton pump inhibitor are administered conjointly.

3. The method of claim 1, wherein the proton pump inhibitor (PPI) is selected from the group consisting of omeprazole, esomeprazole, lansoprazole, pantoprazole, and rabeprazole, and pharmaceutically acceptable salts thereof.

4. The method of claim 1, wherein the proton pump inhibitor (PPI) is omeprazole and the ratio by weight of dexloxiglumide to omeprazole is between 10 and 133.3.

5. The method of claim 1, wherein the proton pump inhibitor (PPI) is lansoprazole and the ratio by weight of dexloxiglumide to lansoprazole is between 10 and 133.3.

* * * * *

UNITED STATES PATENT AND TRADEMARK OFFICE
CERTIFICATE OF CORRECTION

PATENT NO. : 7,863,330 B2  
APPLICATION NO. : 11/424104  
DATED : January 4, 2011  
INVENTOR(S) : Francesco Makovec et al.

Page 1 of 1

It is certified that error appears in the above-identified patent and that said Letters Patent is hereby corrected as shown below:

On the title page, insert as follows:

item --(54) ~~DELOXIGLUMIDE~~ <u>DEXLOXIGLUMIDE</u> AND PROTON PUMP INHIBITORS COMBINATION IN THE TREATMENT OF GASTROINTESTINAL DISORDERS--

Signed and Sealed this

Thirteenth Day of September, 2011

David J. Kappos
*Director of the United States Patent and Trademark Office*

UNITED STATES PATENT AND TRADEMARK OFFICE
CERTIFICATE OF CORRECTION

PATENT NO.       : 7,863,330 B2                                   Page 1 of 1
APPLICATION NO.  : 11/424104
DATED            : January 4, 2011
INVENTOR(S)      : Francesco Makovec et al.

It is certified that error appears in the above-identified patent and that said Letters Patent is hereby corrected as shown below:

On the title page, Item (54) and at Column 1, lines 1-4, title should read as follows:

--DEXLOXIGLUMIDE AND PROTON PUMP INHIBITORS COMBINATION IN THE TREATMENT OF GASTROINTESTINAL DISORDERS--

This certificate supersedes the Certificate of Correction issued September 13, 2011.

Signed and Sealed this
Eleventh Day of October, 2011

David J. Kappos
*Director of the United States Patent and Trademark Office*